United States Patent [19]
Johnson, Jr. et al.

[11] Patent Number: 5,577,998
[45] Date of Patent: Nov. 26, 1996

[54] WALKING BRACE

[75] Inventors: Glenn W. Johnson, Jr., Summit; Henry J. McVicker, Chatham, both of N.J.

[73] Assignee: Aircast, Incorporated, Summit, N.J.

[21] Appl. No.: 383,469

[22] Filed: Feb. 3, 1995

[51] Int. Cl.$^6$ .................................................. A61F 5/00
[52] U.S. Cl. ........................... 602/5; 602/13; 128/882; 128/DIG. 20
[58] Field of Search .................... 128/869, 882, 128/DIG. 20; 602/23, 27, 13, 19

[56] References Cited

U.S. PATENT DOCUMENTS

| | | | |
|---|---|---|---|
| 3,701,349 | 10/1972 | Larson | 602/13 |
| 3,955,565 | 5/1976 | Johnson | 602/13 |
| 4,628,945 | 12/1986 | Johnson | 602/27 |
| 4,948,092 | 8/1990 | Kasper et al. | 251/82 |
| 4,977,891 | 12/1990 | Grim | 602/27 |
| 5,078,128 | 1/1992 | Grim et al. | 602/13 |
| 5,125,400 | 6/1992 | Johnson | 602/27 |
| 5,329,705 | 7/1994 | Grim | 602/27 |
| 5,348,530 | 9/1994 | Grim et al. | 602/13 |
| 5,354,260 | 10/1994 | Cook | 602/27 |
| 5,378,224 | 1/1995 | Billotti | 602/27 |
| 5,407,421 | 5/1994 | Goldsmith | 602/5 |

OTHER PUBLICATIONS

Paul A. Dale, M. D. et al. "A New Concept in Fracture Immobilization". Clinical Orthopaedics. Oct. 1993. vol. 295: 264–269.

*Primary Examiner*—Michael A. Brown
*Attorney, Agent, or Firm*—Jones, Day, Reavis & Pogue

[57] ABSTRACT

A walking brace is disclosed having inflatable air cells to provide therapeutic pressure to the patient's leg and which requires no external equipment or oral inflation tube for reinflation. Each air cell contains a piece of resilient foam, which allows air to come in through an external connection to inflate the air cell when the foam within the air cell expands and the external connection is open. Similarly, when the external connection is open, air leaves the air cell through the external connection in response to pressure on the air cell. However, once the external connection is closed, the air cell maintains its volume of air.

7 Claims, 2 Drawing Sheets

FIG. 4
FIG. 5
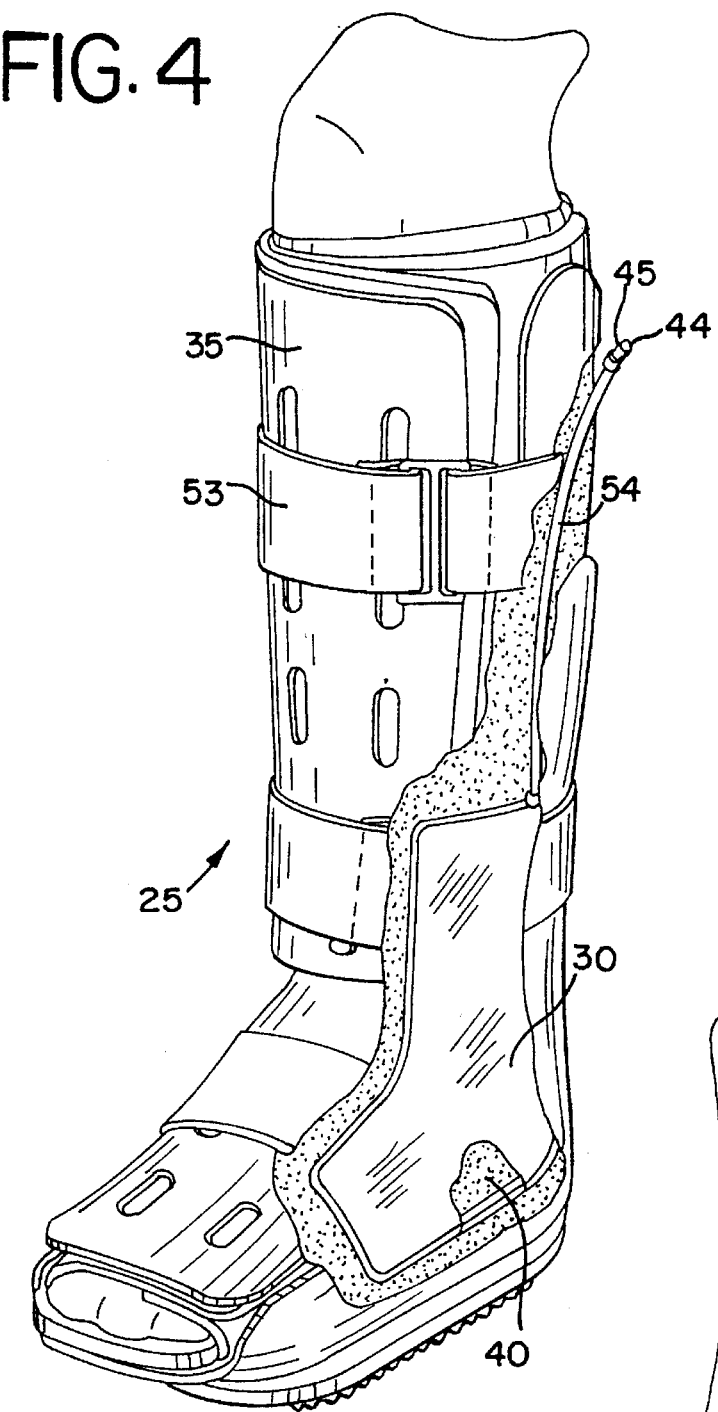
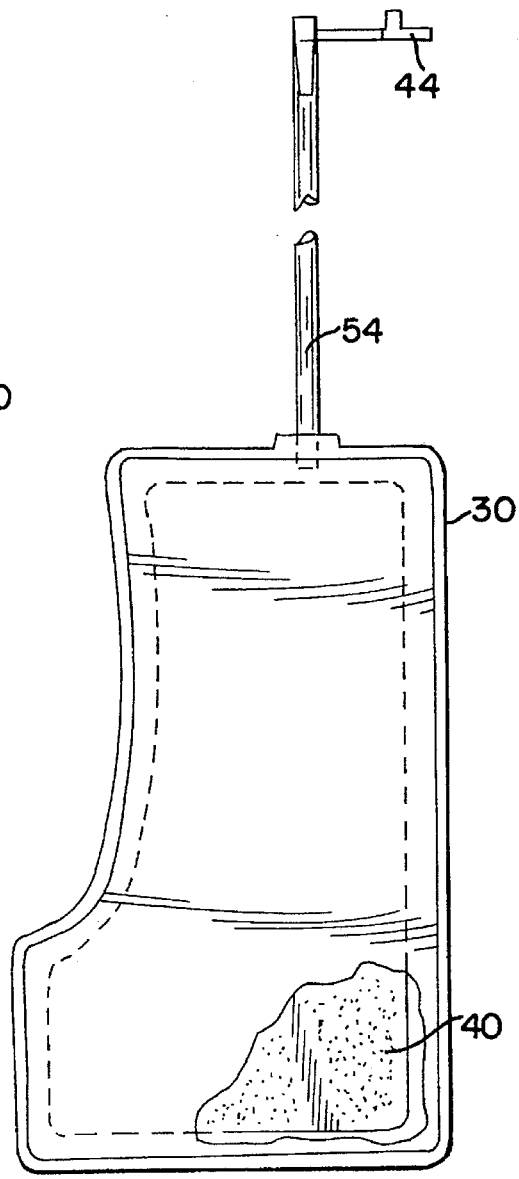

WALKING BRACE

BACKGROUND

1. Field of the Invention

The present invention relates generally to orthopedic devices, and more particularly, to those orthopedic devices known variously as casts, splints, braces, etc. which are especially adapted for immobilizing and/or protecting injured limbs or other parts of the anatomy.

2. Description of Related Art

In the management of certain injuries to the lower extremities such as fractures of the tibia and fibula, malleolar fractures, or severe ankle sprains, it is common to immobilize the lower extremity completely by use of the well-known molded plaster or resin cast. Once the injured extremity has become stable, however, it has been found that recovery may be effected more rapidly by gradually and progressively permitting the extremity to bear weight and undergo other permitted exercises.

For example, an orthopedic brace, such as that disclosed in U.S. Pat. No. 3,955,565, which is assigned to the assignee herein and incorporated herein by reference in its entirety, may be used. This brace features one or more rigid outer shell members having associated therewith an inflatable liner or air cell for engaging a body part or limb. Commercial embodiments of the brace incorporating the invention disclosed in this prior patent are adapted to be fixed about the lower leg and typically comprise a rear outer shell member, a frontal outer shell member, and air cells disposed within the liner of the shell members. Strap fastening means maintain the shell members in engagement with confronting portions of the lower leg whereby each air cell serves as a firm supporting cushion of pressurized air between the irregular contours of the lower leg and the member sidewalls.

This brace construction is capable of stabilizing the ankle and leg while allowing the wearer to walk. Thus, ambulatory functionality and permitted exercises are feasible thereby encouraging more rapid recovery from various injuries to the lower extremity than otherwise would be possible. Moreover, studies have indicated that a pressurized brace yields a stronger fracture than a conventional cast. Dale, P. A. et al., "A New Concept in Fracture Immobilization," *Clinical Orthopedics and Related Research*, 264–269 (1993).

Prior art devices containing air cells required an external pump or oral inflation tube to inflate the air cells. External pumps must be carried by the patient and are necessary to inflate the air cells properly. Oral inflation tubes can be difficult or awkward for some patients to use. Because of the difficulty in reinflating the air cells, some patients may not deflate the air cells as often as they would like or may deflate the air cells and then not reinflate them as soon as desirable for optimum healing.

Unlike the prior art, the present invention provides an apparatus that is easy to inflate without inflation equipment, so that the patient can deflate the air cells when necessary for comfort, and easily reinflate the apparatus later for further therapeutic benefit. For example, on an airplane, the pressure on the patient's leg will increase as the pressure in the cabin decreases. To relieve the discomfort of this additional pressure, the patient can release some air from the air cells to reduce the pressure to a comfortable level during the airplane flight. Then, the patient can easily reinflate the air cells when normal ambient pressure conditions resume.

The present invention allows the patient to reinflate the air cells quickly and without additional inflation equipment, saving both time and the difficulty of carrying such additional equipment.

Thus, one object of the present invention is to provide a walking brace having an effective, inexpensive and manageable means of providing focal compression to the injured portion of the ankle to promote fracture healing and edema management.

It is another object of this invention to provide a removable walking brace containing air cells that provide a comfortable fit with the proper pressure applied to the leg.

It is yet another object of this invention to provide a walking brace containing air cells that the patient can inflate or adjust without an external pump, oral inflating tube or other equipment.

It is also the object of this invention to provide a walking brace that will allow the wearer to change the pressure in the air cells as swelling in the leg varies or as the pressure in the brace changes, such as due to altitude or climate changes.

SUMMARY

The present invention comprises a walking brace having self-inflating air cells which conform to the unique contours of the patient's leg, and provide graduated pressure on the patient's leg to promote the healing process.

The walking brace of this instant invention comprises a hard outer shell. The shell may comprise two mating portions, such as a rear portion and a forward portion. These portions are held around the injured limb in a mating relationship by securing means such as adjustable straps. Each shell portion is padded on its inner surface with a foam liner. Embedded in the foam liner near the patient's ankle are at least one but preferably a pair of self-inflating distal air cells. These air cells cushion and compress the medial and lateral aspects of the ankle. The remainder of the leg is cushioned by the foam liner.

The combination of the foam liner and air cells provide graduated pressure up the patient's leg. For example, the pressure on the ankle from the air cells is higher than the pressure on the calf from the foam liner. Studies have found that graduated pressure promotes the healing process.

Each air cell contains a resilient passive reinflation means, preferably a piece of compressible foam, that in its uncompressed condition is thicker than typical space between the ankle and the shell. A closable connection means extends between each air cell and the exterior of the shell which allows air to enter or leave the air cell when the connection means is open and which prevents movement of air when the connection means is closed.

For a customized fit, the patient's lower leg and ankle are placed in the walking brace with the connection means open. Because the compressible foam and the air cell are thicker than the typical space between the shell and the leg, when the straps are fastened, the leg and ankle compress the air cells and force excess air out of the air cells through the connection means. The patient then closes the connection means, preventing further air from leaving the air cells to provide a constant pressure in the air cell.

If the patient desires greater pressure on his or her ankle, the patient places his or her leg and ankle in the walking brace with the connection means open and presses the ankle towards one side. This allows the air cell on the other side to expand, bringing in additional air. The connection means for this side is then closed. The ankle is then pressed against the closed side, allowing the air cell on the other side to expand, bringing in additional air. The connection means on this second side is then closed. This technique results in more air in each air cell, greater volume in the air cells, and thus greater pressure on the patient's ankle.

One advantage to the present invention is that no external equipment or oral inflation tube is needed to inflate the air cells in the walking brace. By using the natural resilience of foam, air comes in through the external connection means when the foam within the air cell expands. The uncompressed size of the foam is made slightly larger than the typical space between the patient's leg and the shell. Thus, when it is allowed to expand to its uncompressed state, the air cell foam will bring enough air into the air cell to make the air cell larger than needed, which allows the patient to adjust the air cell pressure to an appropriate level.

This simple and inexpensive technique provides custom inflation of the air cells without pumps or oral inflating tubes. Moreover, the resulting walking brace provides graduated compression with the ankle receiving higher pressure and the calf lower pressure.

DESCRIPTION OF THE DRAWINGS

FIG. 4 is a cut away view of the brace of FIG. 1.

FIG. 5 is a plan view of the air cell and the connection means.

DETAILED DESCRIPTION

This invention comprises a walking brace 25 containing at least one inflatable air cell to provide compression along a limb and without using additional equipment to inflate.

Figure 1:
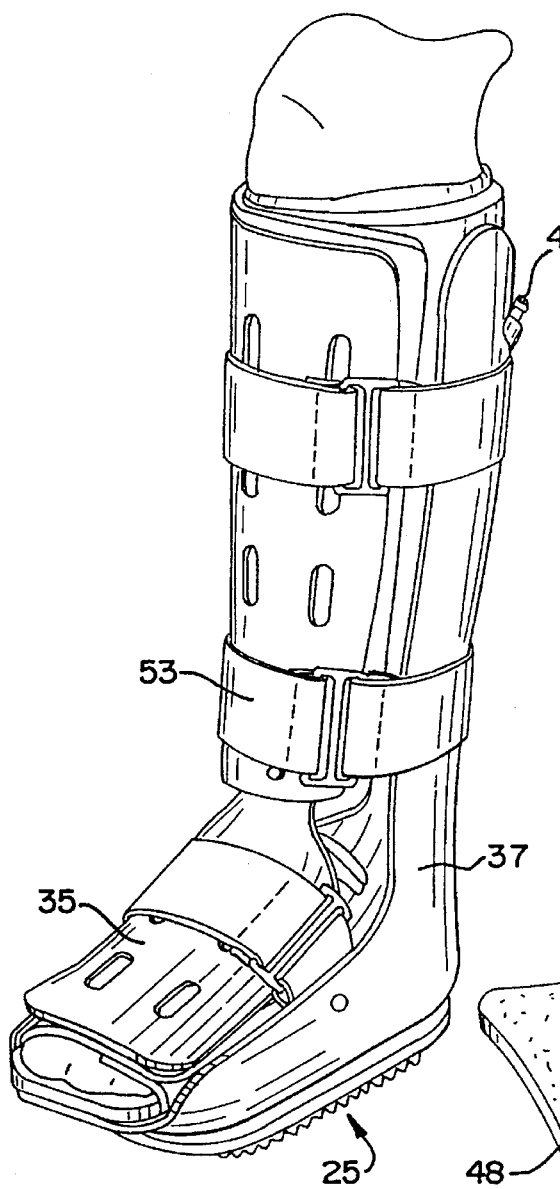
FIG. 1 is a view of the exterior of a preferred embodiment the walking brace.

Referring to FIGS. 1 and 4, a preferred embodiment of the walking brace 25 of the instant invention includes a rigid exterior shell 33 comprising a front shell portion 35, a rear shell portion 37, an interior resilient foam liner 50, a lateral inflatable air cell 30 and a medial inflatable air cell 32. The foam liner 50 advantageously may comprise a lateral foam liner portion 49 and a medial foam liner portion 48. The front shell portion 35 and rear shell portion 37 protect and support the injured leg while the air cells 30, 32 and the foam liners portions 48, 49 cushion the leg against the shell portions 35, 37 and provide pressure on the leg to speed healing and provide greater comfort.

Figure 2:
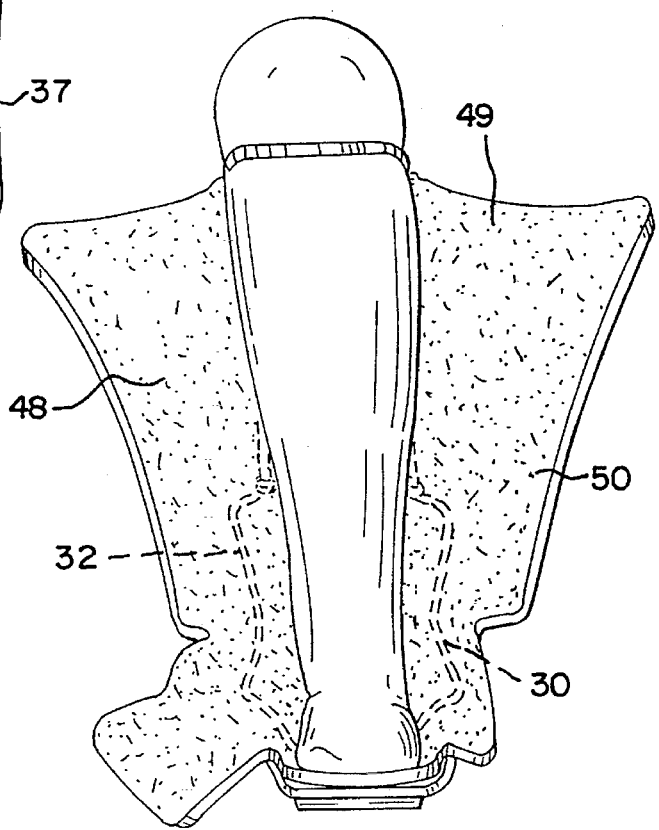
FIG. 2 is a front view of the walking brace of FIG. 1 with the front shell portion off and the foam liner open and with a cut away view of the air cells.

Referring to FIG. 2, the medial air cell 32 and the lateral air cell 30 are gaseously independent, allowing the pressure in each to be adjusted separately. Both air cells 30, 32 are located in the foam liner portions 48, 49 attached to the rear shell portion 37, with the lateral air cell 30 in the lateral foam liner portion 49 and the medial air cell 32 in the medial foam liner portion 48.

The inflatable air cells can be constructed of two sheets of flexible plastic sealed around their perimeter to make a gas impermeable packet. Each air cell 30, 32 contains therein a resilient passive reinflation means, preferably a piece of foam 40, 42. In the fully expanded state, the foam pieces 40, 42 are larger than the typical space between the patient's ankle and the corresponding shell portion.

Referring to FIG. 5, each air cell 30, 32 has a connection means 54 extending from the air cell to the exterior of the shell 33 and terminating in a closable air cell port 44. The connection means 54 links the interior of each air cell 30, 32 with the atmosphere. While the drawings show only the lateral air cell port 44, the medial air cell has a structurally similar connection means and air cell port located on the medial side of the brace 25. The connection means 54 is preferably made of flexible plastic tubing. Preferably both air cell ports 44 extend outside the rear shell portion 37.

Each air cell port 44 is provided with a closable sealing means 45 to trap air in the air cell and maintain the air cell at a constant volume. Sealing means 45 may comprise, for example, a hinged stopper or a rotatable valve. When the sealing means 45 is opened, the foam piece 40, 42, which is larger than the typical space between the patient's ankle and the shell portion 37, within the air cell 30, 32 expands, causing the air cell 30, 32 to expand by bringing air in from its associated air cell port 44.

When the patient puts his or her leg in the walking brace 25 with the air cell ports 44 open, the air cell 30, 32 and the foam piece 40, 42 are compressed by the patient's leg, forcing air out of the air cell 30, 32. The patient then closes the air cell ports 44, sealing the air cell 30, 32 and setting its volume. Once the air cell ports 44 are closed, no more air can escape or enter, thus, when the patient's leg presses against the air cell 30, 32, the air cell 30, 32 resists, putting pressure on the leg.

Figure 3:
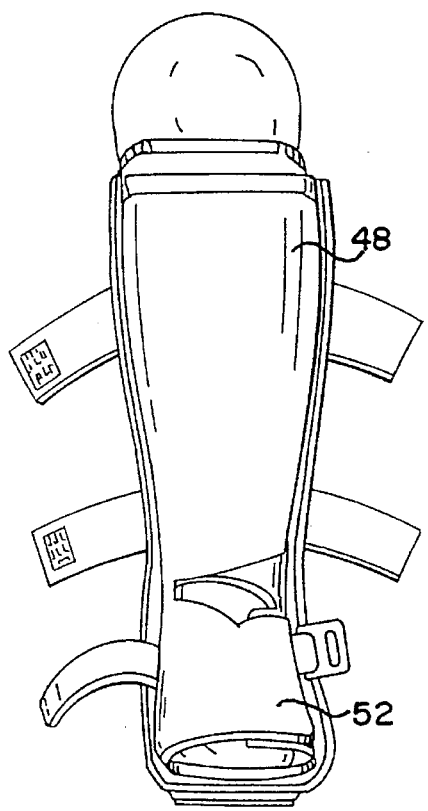
FIG. 3 is a front view of the walking brace of FIG. 1 with the front shell portion off and the foam liner closed.

Before putting his or her leg in the walking brace 25, a patient unseals the sealing means 45 on the lateral and medial air cell ports 44. Referring to FIGS. 2 and 3, the patient then removes the front shell portion 35, opens the lateral foam liner portion 49 and the medial foam liner portion 48 and places his or her lower leg in the rear shell portion 37, heel first. Once the heel is firmly pressed against the rear shell portion 37, the patient closes the lateral and medial air cell ports 44 using the sealing means 45.

Once the air cell ports are closed, the patient wraps the lateral foam liner portion 49 and the medial foam liner portion 48 around his or her leg and foot. The patient then applies the front shell portion 35 over the foam liners 48, 49. Once the front shell portion 35 is in place, the patient wraps the adjustable securing means 53 around the front and rear shell portions 35, 37 to secure them firmly in place. The adjustable securing means 53 preferably comprises flexible straps with hook and loop type fastening means such as VELCRO®.

If the patient desires greater pressure on his or her ankle, the patient first loosens the securing means 53 and opens both air cell ports 44, by opening the sealing means 45. The patient then shifts his or her ankle away from the lateral side, allowing the lateral air cell 30 to expand. The patient then uses the sealing means 45 to close the lateral air cell port 44, trapping the larger amount of air in the lateral air cell 30. Optionally, the patient can repeat this procedure on the opposite side to increase the pressure on the medial cell as well. Since the amount of air in and the volume of one or both the lateral 30 and the medial 32 air cells has increased, the pressure on the patient's ankle is increased.

This invention provides a new walking brace apparatus 25 having self-inflatable air cells. By providing the proper pressure to the air cells of walking brace 25, the patient is ensured a tight yet comfortable fit. By allowing the patient to set the volume of the air cells, the invention enables the patient to fill the air cells with the proper initial pressure. Because the air cells maintain the same volume, they put pressure on the patient's leg as the patient walks, which also increases the internal pressure in the air cells. The foam liner also puts pressure on the patient's leg, although at a lower pressure than the air cells. Thus, the arrangement of the air cells within the walking brace 25 provides graduated pressure to the patient's leg whereby the pressure on the ankle from the air cells is greater than the pressure on the calf from the foam liner portions. The arrangement of air cells in the invention provides higher pressure at the ankle for stability with lower pressures at the calf. This pressure has been found to increase the speed and quality of the healing process and to provide the therapeutic advantages of edema management.

While the invention has been shown and described with respect to a particular embodiment, this is for the purpose of illustration rather than limitation. The inventor envisions, and it will be apparent to those skilled in the art, that other variations and modifications of the embodiment shown and described herein are all within the intended spirit and scope of the invention. Accordingly, the patent is not to be limited in scope and effect to the specific embodiment shown and described nor in any other way that is inconsistent with the extent to which the progress and the art has been advanced by the invention.

We claim:

1. A walking brace for providing therapeutic pressure to the lower leg of a patient, said brace comprising:

an exterior shell adapted to fit substantially around the lower leg of a patient;

an interior resilient liner to cushion the leg;

at least one inflatable air cell located in said interior liner for providing an adjustable desired therapeutic pressure to said leg;

connection means movable between a closed condition and an open condition which links the interior of said air cell with the atmosphere;

passive reinflation means within said air cell for cooperating with said connection means when a user opens said connection means to facilitate reinflation of said air cell without an additional active reinflation means and deflation of said air cell when the user applies pressure to said air cell to deflate said air cell to a desired lower pressure; said passive reinflation means maintaining said air cell at a desired pressure when the user closes said connection means; and means for securing said walking brace about the lower leg such that said air cell puts pressure on the lower leg.

2. The walking brace of claim 1 wherein said reinflation means is foam that expands when said connection means is unsealed causing air to enter said at least one air cell through said connection means and to reinflate said at least one air cell.

3. The walking brace of claim 1 wherein said reinflation means is thicker than the typical space between said exterior shell and the lower leg.

4. The walking brace of claim 1 wherein said connection means comprises a plastic tube.

5. The walking brace of claim 1 wherein, when fully inflated, said at least one air cell is thicker than the typical space between said exterior shell and the lower leg.

6. The walking brace of claim 1 comprising at least two said air cells.

7. The walking brace of claim 6 wherein each of said air cell has a separate connection means and separate sealing means.

* * * * *